United States Patent
Fujimoto et al.

(10) Patent No.: US 11,918,400 B2
(45) Date of Patent: Mar. 5, 2024

(54) CONTROL DEVICE, CONTROL METHOD, AND CONTROL PROGRAM

(71) Applicant: FUJIFILM CORPORATION, Tokyo (JP)

(72) Inventors: Yoshie Fujimoto, Kanagawa (JP); Shinichiro Konno, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 247 days.

(21) Appl. No.: 17/486,954

(22) Filed: Sep. 28, 2021

(65) Prior Publication Data

US 2022/0096032 A1  Mar. 31, 2022

(30) Foreign Application Priority Data

Sep. 30, 2020 (JP) ................. 2020-166466

(51) Int. Cl.
*A61B 6/00* (2006.01)
*A61B 6/04* (2006.01)
(Continued)

(52) U.S. Cl.
CPC ............ *A61B 6/502* (2013.01); *A61B 6/0414* (2013.01); *A61B 6/542* (2013.01);
(Continued)

(58) Field of Classification Search
CPC .. A61B 6/00; A61B 6/04; A61B 6/502; A61B 6/542; A61B 6/0414; A61B 6/0492;
(Continued)

(56) References Cited

U.S. PATENT DOCUMENTS 7,732,775 B2 *  6/2010  Kashiwagi ........... A61B 6/0414
                                                        250/363.05
2010/0054402 A1   3/2010  Fischer et al.
(Continued)

FOREIGN PATENT DOCUMENTS

JP    H02-166437 A    6/1990
JP    2007-236805 A    9/2007
(Continued)

OTHER PUBLICATIONS

English language translation of the following: Office action dated May 9, 2023 from the JPO in a Japanese patent application No. 2020-166466 corresponding to the instant patent application. This office action translation is submitted now in order to supplement the understanding of the cited references which are being disclosed in the instant Information Disclosure Statement.

*Primary Examiner* — Jurie Yun
(74) *Attorney, Agent, or Firm* — SOLARIS Intellectual Property Group, PLLC

(57) ABSTRACT

A control device including: at least one processor that is configured to detect whether or not compression of a breast by a compression member in a mammography apparatus is completed and perform control to direct an image projection unit, which projects a projection image onto a projection surface of the compression member, to stop the projection of the projection image onto the projection surface in a case in which it is detected that the compression is completed.

10 Claims, 8 Drawing Sheets

(51) Int. Cl.
 *G03B 21/20* (2006.01)
 *G06T 7/00* (2017.01)
(52) U.S. Cl.
 CPC ........ *G03B 21/2053* (2013.01); *G06T 7/0012* (2013.01); *G06T 2207/30068* (2013.01)
(58) Field of Classification Search
 CPC .... A61B 6/54; A61B 6/46; G06T 7/00; G06T 7/0012; G06T 2207/30068; G03B 21/20; G03B 21/2053; G03B 21/10; G03B 42/02
 See application file for complete search history.

(56) References Cited

U.S. PATENT DOCUMENTS

| | | |
|---|---|---|
| 2016/0316184 A1 | 10/2016 | Kim et al. |
| 2017/0172531 A1 | 6/2017 | Sugiyama et al. |
| 2017/0367671 A1 | 12/2017 | Arai et al. |

FOREIGN PATENT DOCUMENTS

| | | |
|---|---|---|
| JP | 2008-086389 A | 4/2008 |
| JP | 2009-291336 A | 12/2009 |
| JP | 2010-253263 A | 11/2010 |
| JP | 2011-104149 A | 6/2011 |
| JP | 2017-113540 A | 6/2017 |
| JP | 2017-225634 A | 12/2017 |

\* cited by examiner

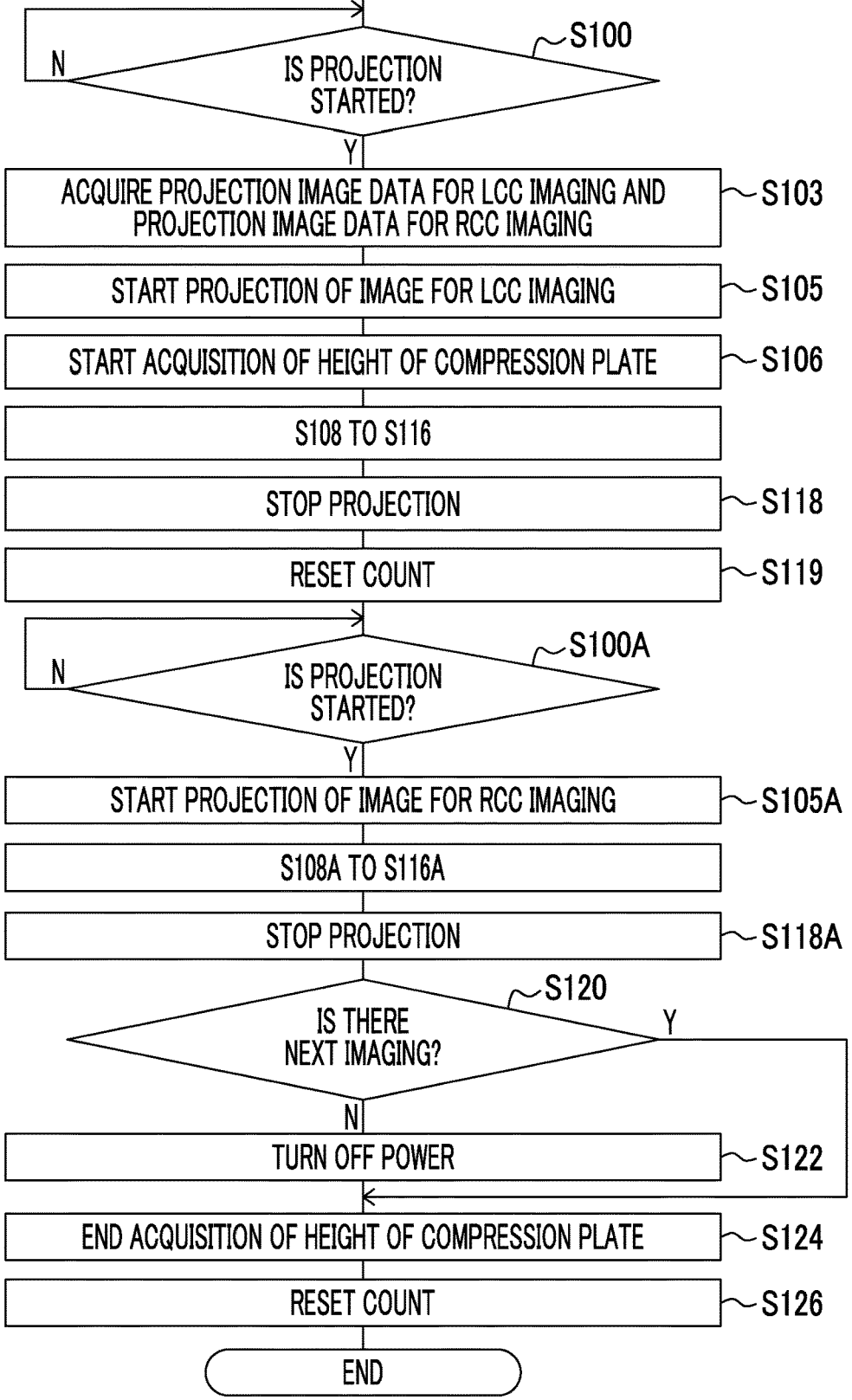

CONTROL DEVICE, CONTROL METHOD, AND CONTROL PROGRAM

CROSS-REFERENCE TO RELATED APPLICATION

The present application claims priority under 35 U.S.C. § 119 to Japanese Patent Application No. 2020-166466 filed on Sep. 30, 2020. The above application is hereby expressly incorporated by reference, in its entirety, into the present application.

BACKGROUND

Technical Field

The present disclosure relates to a control device, a control method, and a non-transitory computer-readable storage medium storing a control program.

Description of the Related Art

A mammography apparatus is known which irradiates a breast compressed by a compression member with radiation to capture a radiographic image. In a case in which imaging is performed, information or the like for assisting the imaging may be displayed. For example, JP2008-086389A discloses a technique that displays a skin line of the breast on an LCD and displays a projection image thereof on a projection surface of a compression member.

However, in a case in which the projection image is projected in the mammography apparatus, the amount of heat generated by an image projection unit that projects the projection image becomes larger as the projection time becomes longer. In some cases, heat accumulation occurs in the mammography apparatus. On the other hand, in a case in which the projection time of the projection image is short, it may be difficult to position the breast in an appropriate state. However, in the technique disclosed in JP2008-086389A, in a case in which the projection of the projection image onto the projection surface of the compression member is automatically stopped, it may be difficult to stop the projection of the projection image at an appropriate timing.

The present disclosure has been made in view of the above-mentioned problems, and an object of the present disclosure is to provide a control device, a control method, and a non-transitory computer-readable storage medium storing a control program that can automatically stop the projection of a projection image onto a projection surface of a compression member at an appropriate timing.

SUMMARY

In order to achieve the above object, according to a first aspect of the present disclosure, there is provided a control device comprising at least one processor. The processor is configured to detect whether or not compression of a breast by a compression member in a mammography apparatus is completed and perform control to direct an image projection unit, which projects a projection image onto a projection surface of the compression member, to stop the projection of the projection image onto the projection surface in a case in which it is detected that the compression is completed.

According to a second aspect of the present disclosure, in the control device according to the first aspect, the case in which the compression is completed may be a case in which a gap between an imaging table on which the breast is positioned and the compression member does not change for a predetermined period or more.

According to a third aspect of the present disclosure, in the control device according to the first aspect, the case in which the compression is completed may be a case in which a thickness of the breast compressed by the compression member does not change for a predetermined period or more.

According to a fourth aspect of the present disclosure, in the control device according to the first aspect, the case in which the compression is completed may be a case in which a compression pressure of the compression member against the breast does not change for a predetermined period or more.

According to a fifth aspect of the present disclosure, in the control device according to the first aspect, the processor may receive an irradiation start instruction to start irradiation of the breast with radiation, and the case in which the compression is completed may be a case in which the processor receives the irradiation start instruction.

According to a sixth aspect of the present disclosure, in the control device according to the fifth aspect, after performing the control to stop the projection, the processor may perform control to direct the mammography apparatus to start the irradiation of the breast with the radiation.

According to a seventh aspect of the present disclosure, in the control device according to the first aspect, the processor may perform control to turn off the image projection unit to stop the projection of the projection image onto the projection surface.

According to an eighth aspect of the present disclosure, in the control device according to the seventh aspect, the processor may perform control to stop the projection of the projection image onto the projection surface without turning off the image projection unit in a case in which an instruction for next imaging using the mammography apparatus is received.

According to a ninth aspect of the present disclosure, in the control device according to the first aspect, in a case in which the mammography apparatus captures each of a series of a plurality of radiographic images, the processor may further perform control to direct the image projection unit to stop the projection of the projection image onto the projection surface between imaging operations corresponding to each of the plurality of radiographic images and may further perform control to project, onto the projection surface, the projection image corresponding to each of the imaging operations corresponding to the plurality of radiographic images.

Further, in order to achieve the above object, according to a tenth aspect of the present disclosure, there is provided a control method comprising: detecting whether or not compression of a breast by a compression member in a mammography apparatus is completed; and performing control to direct an image projection unit, which projects a projection image onto a projection surface of the compression member, to stop the projection of the projection image onto the projection surface in a case in which it is detected that the compression is completed.

Further, in order to achieve the above object, according to an eleventh aspect of the present disclosure, there is provided a non-transitory computer-readable storage medium storing a control program that causes a computer to perform a process comprising: detecting whether or not compression of a breast by a compression member in a mammography apparatus is completed; and performing control to direct an image projection unit, which projects a projection image onto a projection surface of the compression member, to stop the projection of the projection image onto the projection surface in a case in which it is detected that the compression is completed.

According to the present disclosure, it is possible to automatically stop the projection of the projection image onto the projection surface of the compression member at an appropriate timing.

BRIEF DESCRIPTION OF THE DRAWINGS

Exemplary embodiments according to the technique of the present disclosure will be described in detail based on the following figures, wherein:

FIG. 10 is a flowchart illustrating an example of the flow of a projection control process according to a fourth embodiment.

DETAILED DESCRIPTION

Hereinafter, embodiments of the present disclosure will be described in detail with reference to the drawings. In addition, each of the embodiments does not limit the present disclosure.

First Embodiment

Figure 1:
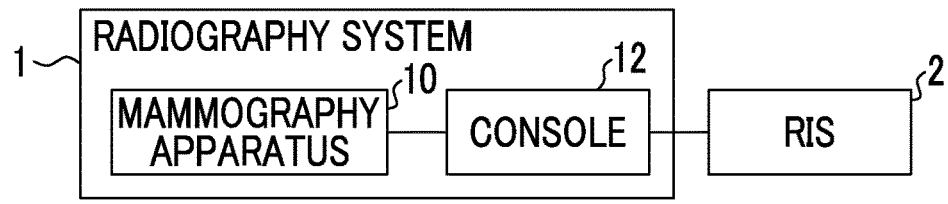
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of a control device according to the present disclosure.

Figure 2A:
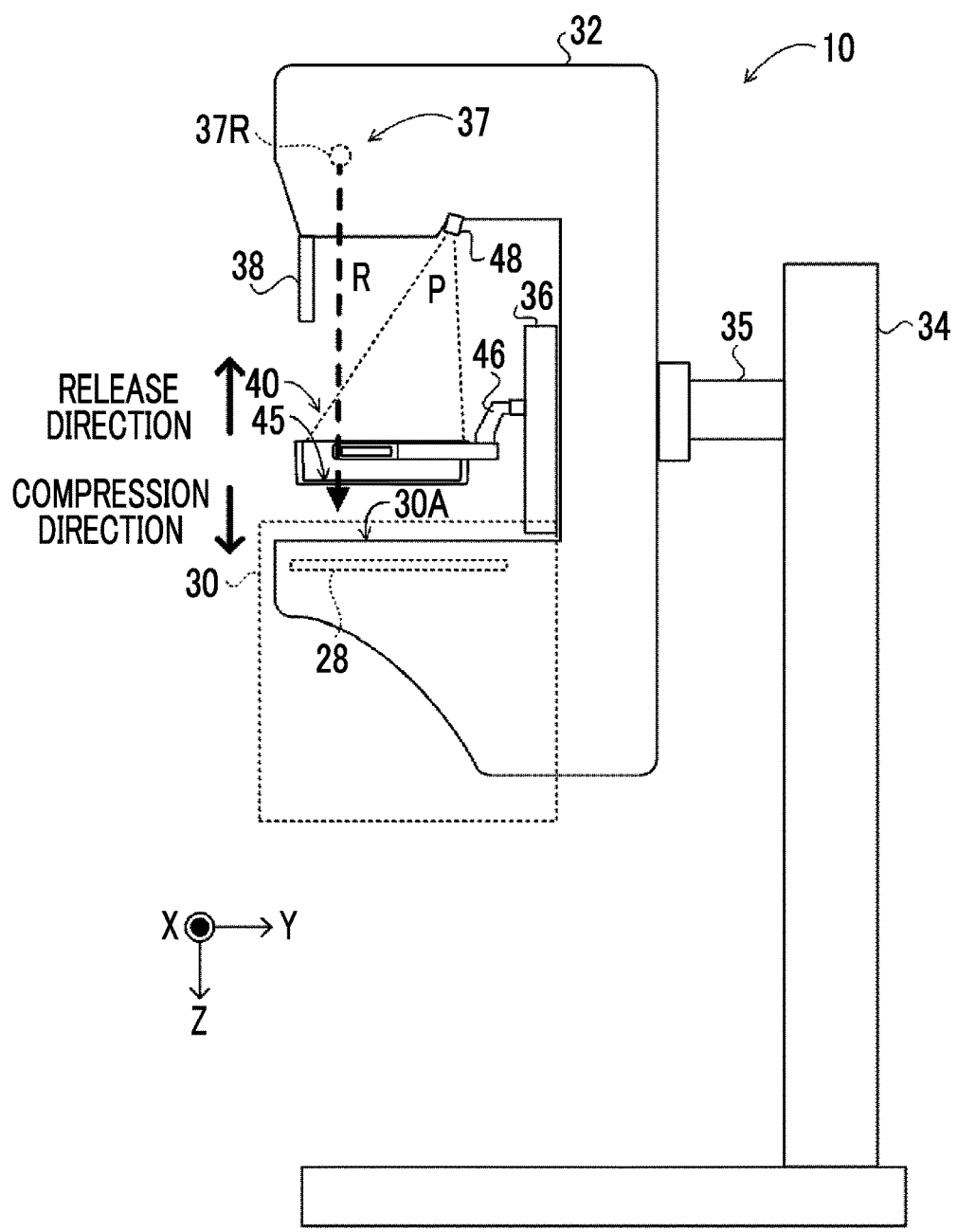
FIG. 2A is a side view illustrating an example of the outward appearance of a mammography apparatus according to the embodiment.
Figure 3:
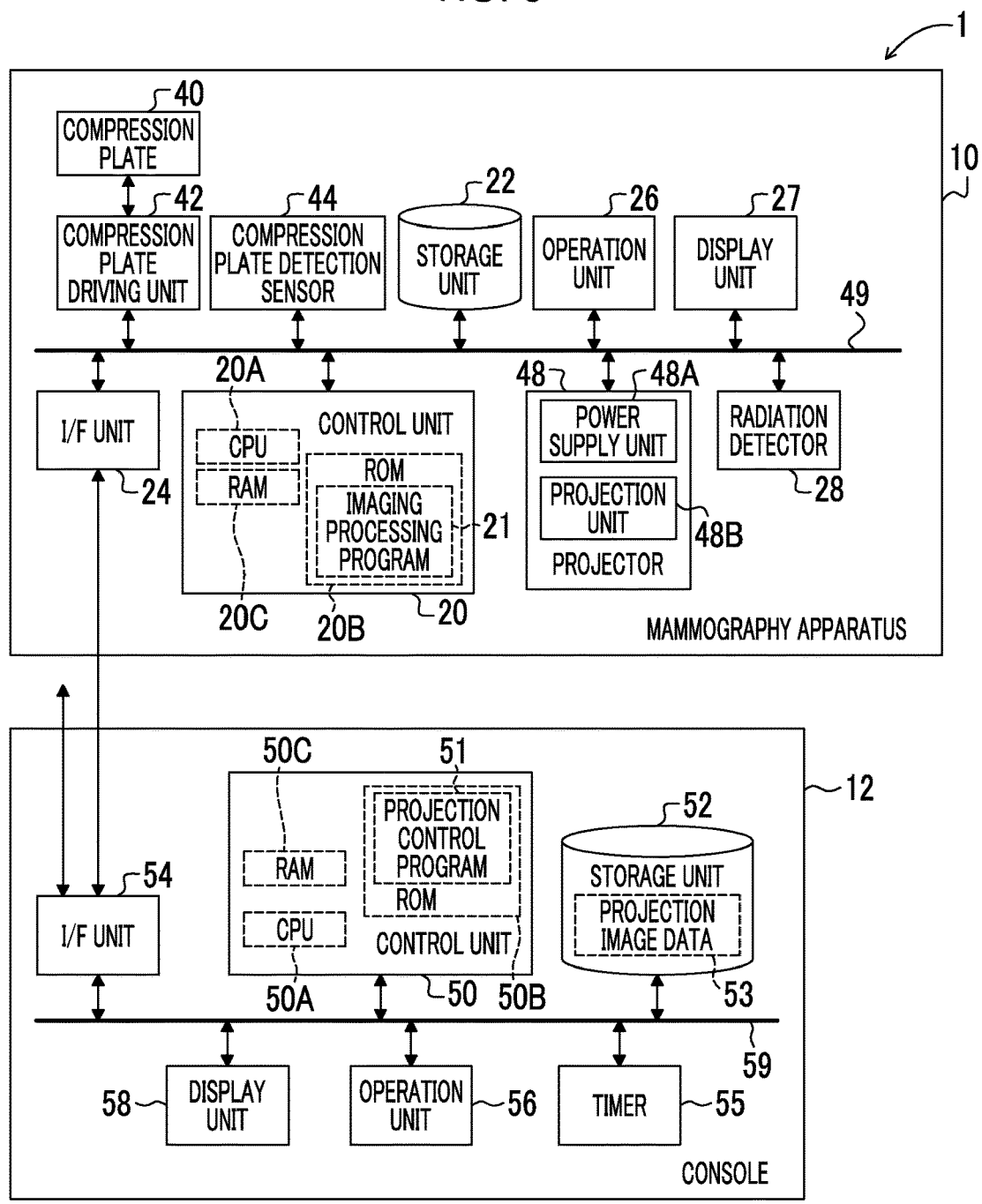
FIG. 3 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates a breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. The face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves a compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. The reason why the breast is compressed by the compression plate 40 is, for example, to expand the overlap of the mammary gland tissues to make it easy to determine whether the mammary gland tissue is a benign lesion or a malignant lesion, to suppress the blurring of a radiographic image to make it easy to see a mammary gland structure or the like, to fix the breast in place to suppress the body movement of the subject, and to decrease the thickness of the breast to reduce the radiation exposure of the breast. As illustrated in FIG. 2A, for the movement direction of the compression plate 40, the direction in which the breast is compressed, that is, the direction in which the compression plate 40 approaches the imaging surface 30A, is referred to as a "compression direction", and the direction in which the compression of the breast is released, that is, the direction in which the compression plate 40 approaches the radiation emitting unit 37, is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2B:
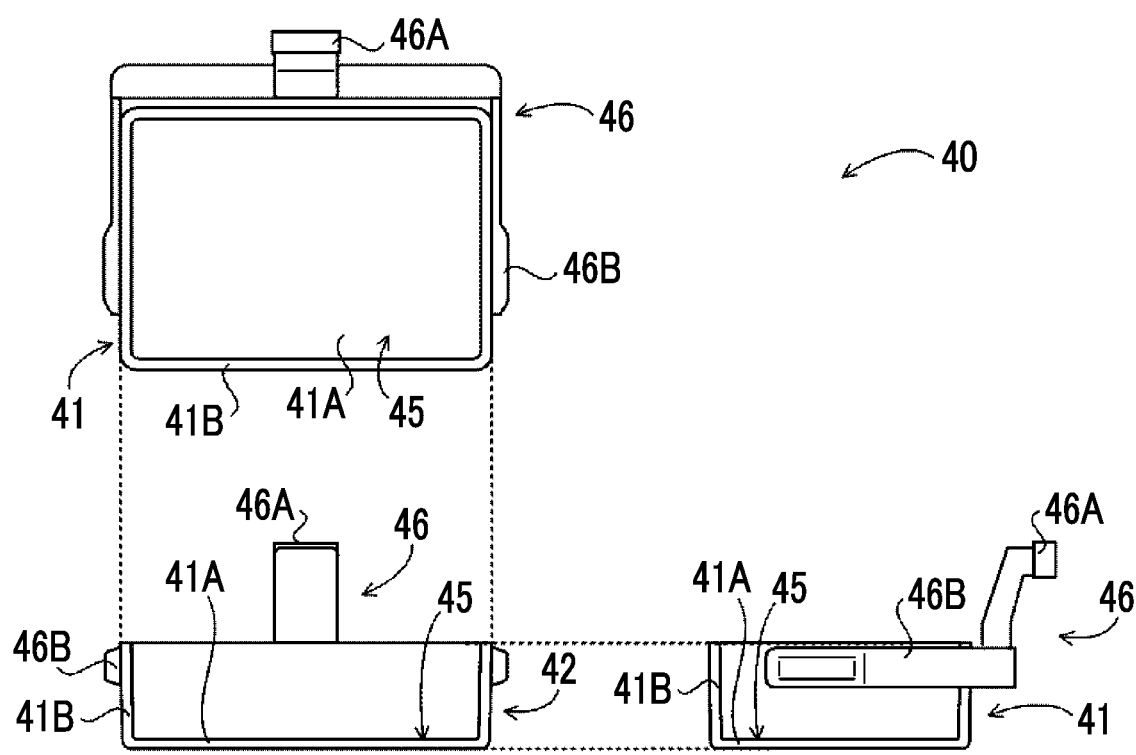
FIG. 2B is a three-view diagram illustrating an example of a compression plate according to the embodiment.

As a specific example, the compression plate 40 that can be attached to the mammography apparatus 10 according to this embodiment will be described with reference to FIG. 2B. FIG. 2B is a three-view diagram illustrating an example of the compression plate 40 according to this embodiment. The three-view diagram illustrated in FIG. 2B includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2B, the compression plate 40 according to this embodiment includes a compression portion 41 and a support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this aspect. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from a control unit 20 which will be described below. Further, the projection image P is projected from the projection unit 48B onto the projection surface 45 of the compression plate 40 in response to an instruction from the control unit 20.

Furthermore, the control unit 20, a storage unit 22, an interface (I/F) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by the radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, a timer 55, the operation unit 56, and a display unit 58. The control unit 50, the storage unit 52, the I/F unit 54, the timer 55, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a projection control program 51 (which will be described below) executed by the CPU 50A are stored in the ROM 50B in advance. The RAM 50C temporarily stores various kinds of data. The CPU 50A according to this embodiment is an example of a processor according to the present disclosure. The projection control program 51 according to this embodiment is an example of a control program according to the present disclosure.

The storage unit 52 stores, for example, projection image data 53, the image data of the radiographic image captured by the mammography apparatus 10, and various other kinds of information. An HDD or an SSD is given as a specific example of the storage unit 52.

The operation unit 56 is used by the user to input, for example, instructions which are related to the capture of a radiographic image and which include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication. The timer 55 starts and stops counting in response to an instruction from the control unit 50.

Figure 4:
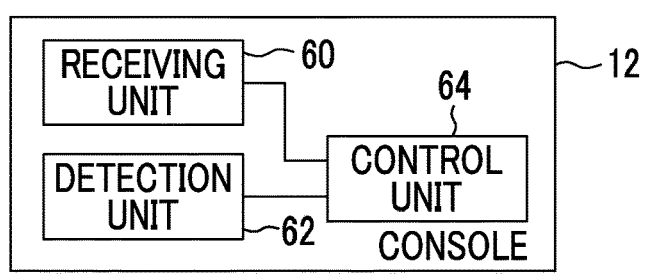
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a receiving unit 60, a detection unit 62, and a control unit 64. For example, in the console 12 according to this embodiment, the CPU 50A of the control unit 50 executes the projection control program 51 stored in the ROM 50B to function as the receiving unit 60, the detection unit 62, and the control unit 64.

The receiving unit 60 has a function of receiving a projection start instruction for starting the projection of the projection image P onto the projection surface 45. For example, in this embodiment, in a case in which the user wants to start the projection of the projection image P onto the projection surface 45, the user instructs the start of the projection through the operation unit 26 of the mammography apparatus 10. The mammography apparatus 10 outputs a projection start instruction signal through the I/F unit 24. In a case in which the projection start instruction signal is input to the console 12, the receiving unit 60 receives the projection start instruction for starting the projection of the projection image P. The receiving unit 60 outputs projection start information indicating that the projection start instruction has been received to the control unit 64.

The detection unit 62 has a function of detecting whether or not the compression of the breast by the compression plate 40 is completed. For example, in this embodiment, in a case in which the compression of the breast is completed, the user stops the movement of the compression plate 40. The thickness of the breast gradually decreases until the compression is completed after the compression plate 40 comes into contact with the breast. However, in a case in which the movement of the compression plate 40 is stopped, the thickness of the breast compressed by the compression plate 40 hardly changes. That is, in a case in which the compression of the breast is completed, the thickness of the breast compressed by the compression plate 40 does not change. The thickness of the breast compressed by the compression plate 40 corresponds to a gap between the compression plate 40 and the imaging table 30 and also corresponds to the height from the imaging surface 30A of the imaging table 30 to the compression plate 40. Therefore, the detection unit 62 according to this embodiment detects a case in which the height from the imaging surface 30A of the imaging table 30 to the compression plate 40 does not change for a predetermined period or more as a case in which the compression is completed. In addition, in the following description, the height from the imaging surface 30A of the imaging table 30 to the compression plate 40 is simply referred to as "the height of the compression plate 40".

In a case in which the compression plate 40 is moved by the compression plate driving unit 42, the control unit 20 of the mammography apparatus 10 outputs a movement signal indicating the movement of the compression plate 40 and the movement direction of the compression plate 40 to the console 12 through the I/F unit 24. The detection unit 62 according to this embodiment derives the amount of movement of the compression plate 40 in the compression direction or the release direction by the compression plate driving unit 42 of the mammography apparatus 10 on the basis of the movement signal input to the console 12 to derive the height of the compression plate 40. Then, the detection unit 62 detects a case in which the height of the compression plate 40 does not change for a predetermined period or more as the case in which the compression is completed. In a case in which the detection unit 62 detects that the compression of the breast by the compression plate 40 is completed, it outputs compression completion information to the control unit 64.

Further, in this embodiment, the detection that the height of the compression plate 40 does not change is not limited to the case in which the height does not change at all, and a change in the height which is regarded as an error is ignored. Furthermore, the predetermined period is not particularly limited. For example, in this embodiment, the period is a period of time that is at least longer than the time until the compression plate 40 is moved from an initial position to the position where it comes into contact with the breast having a standard thickness. Examples of the initial position of the compression plate 40 include a position that is closest to the radiation source 37R among the positions of the compression plate 40 attached to the compression unit 36 of the mammography apparatus 10.

In addition, as described above, in this embodiment, the aspect in which the detection unit 62 of the console 12 detects the height of the compression plate 40 has been described. However, the present disclosure is not limited to this aspect, and the mammography apparatus 10 may detect the height of the compression plate 40. In this case, the detection unit 62 acquires a height signal indicating the height of the compression plate 40 as a detection result from the mammography apparatus 10.

Further, the detection unit 62 according to this embodiment has a function of detecting the type of the compression plate 40 attached to the compression unit 36 of the mammography apparatus 10. As described above, in the mammography apparatus 10, the compression plate detection sensor 44 reads the compression plate identifier of the compression plate 40 having the support portion 46 attached to the compression unit 36. Therefore, the detection unit 62 according to this embodiment acquires the compression plate identifier read by the compression plate detection sensor 44 from the mammography apparatus 10 and outputs the acquired compression plate identifier to the control unit 64.

The control unit 64 has a function of performing control to project the projection image P onto the projection surface 45 in a case in which the receiving unit 60 receives the projection start instruction. Specifically, in a case in which the projection start information is input from the receiving unit 60, the control unit 64 outputs a start control signal for directing the projector 48 to start the projection of the projection image P and the projection image data 53 indicating the projection image P corresponding to the compression plate identifier input from the detection unit 62 to the mammography apparatus 10 through the I/F unit 54.

Further, the control unit 64 has a function of performing control to stop the projection of the projection image P onto the projection surface 45 by the projector 48 of the mammography apparatus 10 in a case in which the detection unit 62 detects that the compression is completed. Specifically, in a case in which the compression completion information is input from the detection unit 62, the control unit 64 outputs the projection image data 53 indicating a stop control signal for stopping the projection of the projection image P by the projector 48 to the mammography apparatus 10 through the I/F unit 54.

Figure 5:
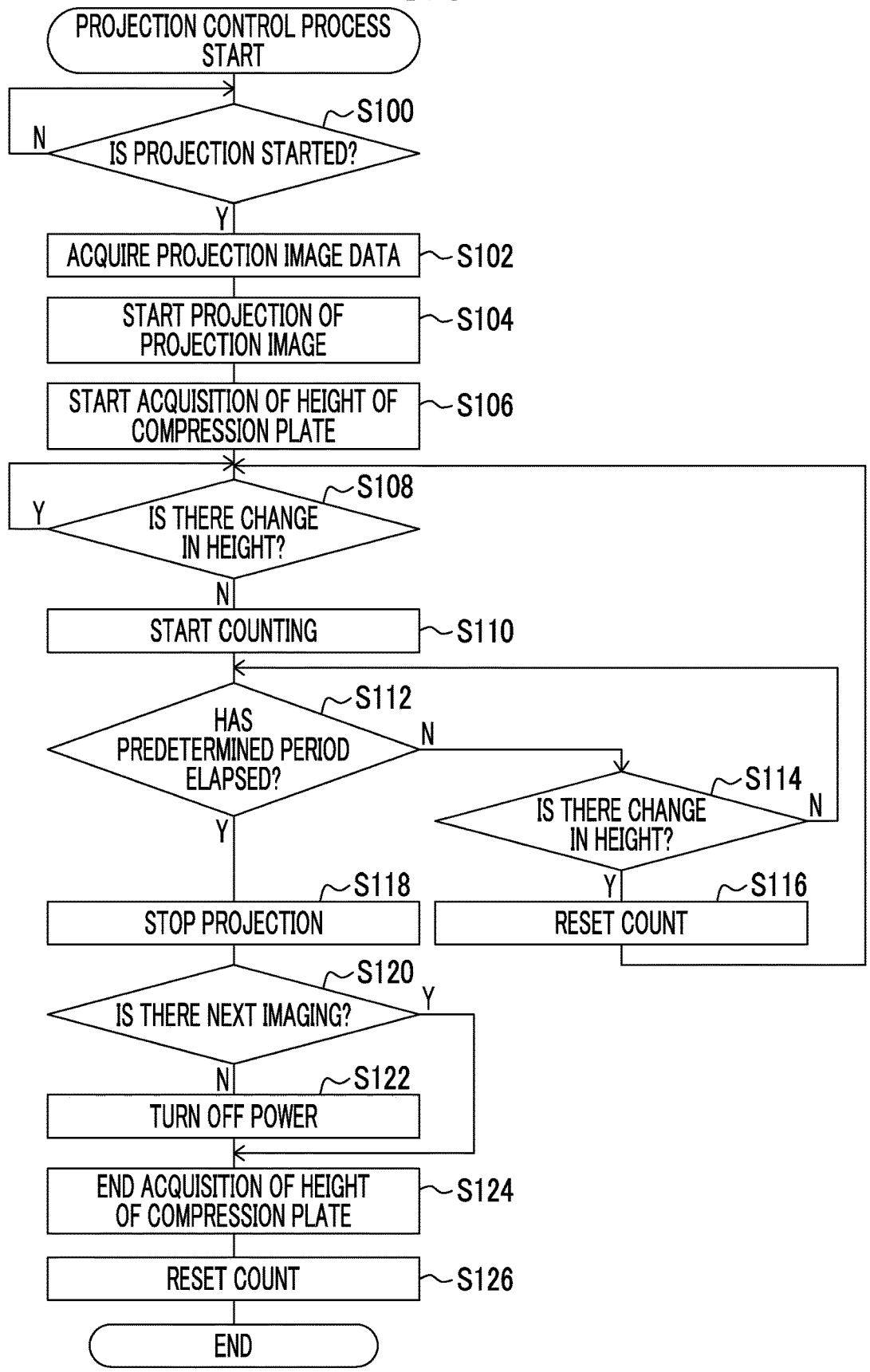
FIG. 5 is a flowchart illustrating an example of the flow of a projection control process according to a first embodiment.

Next, the operation of the console 12 in the projection of the projection image P by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, a projection control process illustrated in FIG. 5 is performed. In the console 12 according to this embodiment, for example, the CPU 50A of the control unit 50 executes the projection control program 51 stored in the ROM 50B to perform the projection control process whose example is illustrated in FIG. 5. FIG. 5 is a flowchart illustrating an example of the flow of the projection control process performed in the console 12 according to this embodiment.

In Step S100 of FIG. 5, the control unit 64 determines whether or not to start the projection of the projection image P. As described above, the determination result in Step S100 is "No" until the receiving unit 60 receives the projection start instruction signal. On the other hand, in a case in which the receiving unit 60 receives the projection start instruction signal, the determination result in Step S100 is "Yes", and the process proceeds to Step S102.

In Step S102, the control unit 64 acquires the projection image data 53 corresponding to the compression plate identifier input from the detection unit 62 from the storage unit 52. For example, a projection image for guiding the positioning of the breast is applied as the projection image P according to this embodiment. Specifically, a projection image projected from the projector 48 in order to display an image for guiding at least one of the shape or position of the breast compressed by the compression plate 40 on the projection surface 45 of the compression plate 40 is applied as the projection image P. For example, in this embodiment, an image indicating the skin line of the breast and the position of the nipple in a case in which a standard breast corresponding to the type of the compression plate 40 or the like is compressed to an ideal state is applied as the image for guiding at least one of the shape or position of the breast.

In some cases, the size of the compression portion 41 and the size of the projection surface 45 vary depending on the type of the compression plate 40. Therefore, in this embodiment, the projection image P corresponding to the type of the compression plate 40 is projected from the projector 48. For example, in this embodiment, a plurality of projection image data items indicating the projection images P corresponding to the types of the compression plates 40 are stored as the projection image data 53 in the storage unit 52 so as to be associated with the compression plate identifiers. Therefore, the control unit 64 acquires the projection image data 53 corresponding to the compression plate identifier input from the detection unit 62 from the storage unit 52 and outputs the projection image data 53 to the mammography apparatus 10 through the I/F unit 54.

Figure 6:
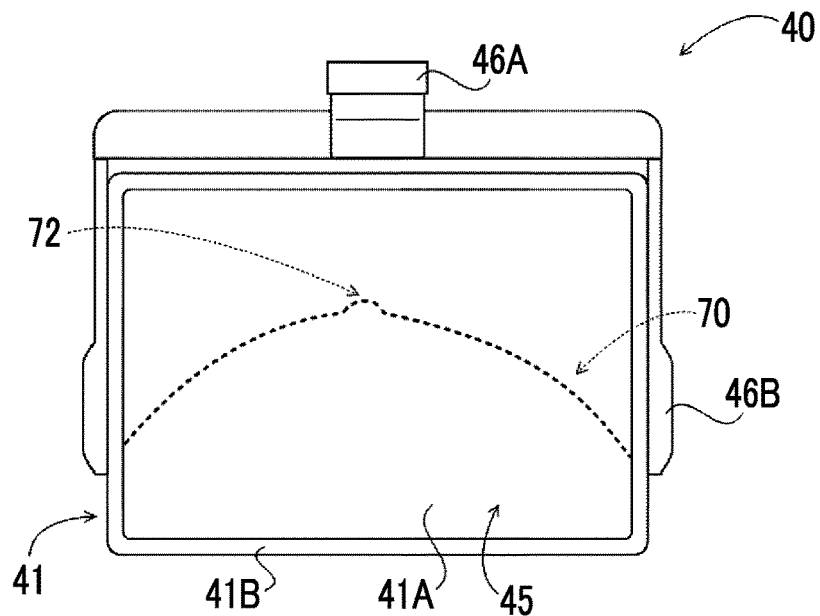
FIG. 6 is a diagram illustrating an example of a state displayed by a projection image projected onto a projection surface of the compression plate.

Then, in Step S104, the control unit 64 outputs the projection image data 53 acquired in Step S102 to the mammography apparatus 10 through the I/F unit 54. In the mammography apparatus 10, in a case in which the projection image data 53 is input, the control unit 20 performs control to direct the projection unit 48B of the projector 48 to project the projection image P corresponding to the projection image data 53. A display image corresponding to the projection image P is displayed on the projection surface 45 of the compression plate 40 attached to the compression unit 36 of the mammography apparatus 10 by this control. In this embodiment, as described above, an image indicating the skin line of the breast and the position of the nipple is displayed on the projection surface 45 of the compression plate 40. FIG. 6 illustrates an example of a skin line 70 and a position 72 of the nipple displayed on the projection surface 45 of the compression plate 40. The user compresses the breast of the subject positioned with reference to the displayed skin line and the displayed position of the nipple with the compression plate 40.

Then, in Step S106, the detection unit 62 starts to acquire the height of the compression plate 40. Specifically, as described above, the detection unit 62 starts to acquire the movement signal output from the mammography apparatus 10 and starts to derive the height of the compression plate 40 on the basis of the acquired movement signal. After that, the detection unit 62 repeats the acquisition of the movement signal and the derivation of the height of the compression plate 40 at predetermined intervals.

Then, in Step S108, the detection unit 62 determines whether or not the height of the compression plate 40 has changed. The determination result in Step S108 is "Yes" until the height of the compression plate 40 derived on the basis of the movement signal does not change. On the other hand, in a case in which the height of the compression plate 40 derived on the basis of the movement signal has not changed, the determination result in Step S108 is "No", and the process proceeds to Step S110.

In Step S110, the detection unit 62 directs the timer 55 to start counting. Then, in Step S112, the detection unit 62 determines whether or not a predetermined period has elapsed as described above. In a case in which the detection unit 62 determines that the predetermined period has not elapsed with reference to the count of the timer 55, the determination result in Step S112 is "No", and the process proceeds to Step S114.

In Step S114, the detection unit 62 determines whether or not the height of the compression plate 40 has changed. In a case in which the height of the compression plate 40 derived on the basis of the movement signal has changed, the determination result in Step S114 is "Yes", and the process proceeds to Step S116. In Step S116, the detection unit 62 stops the counting of the timer 55 and resets the count. Then, the detection unit 62 returns to Step S108 and repeats the above-mentioned process. On the other hand, in a case in which the height of the compression plate 40 derived on the basis of the movement signal has not changed in Step S114, the determination result in Step S114 is "No", and the process returns to Step S112.

In this way, the processes in Steps S108 to S116 are repeated until a predetermined period elapses after the height of the compression plate 40 does not change. In a case in which the compression of the breast by the compression plate 40 is completed, as described above, the movement of the compression plate 40 is stopped. Therefore, the height of the compression plate 40 does not change. In a case in which the predetermined period has elapsed since the height of the compression plate 40 did not change, the determination result in Step S112 is "Yes", and the process proceeds to Step S118. In this case, the compression completion information is output from the detection unit 62 to the control unit 64 as described above.

In Step S118, as described above, the control unit 64 outputs the stop control signal for stopping the projection of the projection image P by the projector 48 to the mammography apparatus 10 through the I/F unit 54. In the mammography apparatus 10, in a case in which the stop control signal is input, the control unit 20 stops the projection of the projection image P by the projection unit 48B of the projector 48. Specifically, the emission of projection light for projecting the projection image P is stopped.

Then, in Step S120, the control unit 64 determines whether or not an instruction for the next imaging is received. In this embodiment, examples of the case in which the instruction for the next imaging is received include a case in which the console 12 acquires an imaging order for the next imaging from the RIS and a case in which the previous imaging is performed in a state in which an imaging order for continuously performing MLO imaging and CC imaging is executed. On the other hand, in a case in which the instruction for the next imaging is received, the determination result in Step S120 is "Yes", and the process proceeds to Step S124. In a case in which the instruction for the next imaging is not received, the determination result in Step S120 is "No", and the process proceeds to Step S122.

In Step S122, the control unit 64 turns off the projector 48. Specifically, the control unit 64 outputs a power-off signal to the mammography apparatus 10 through the I/F unit 54. In a case in which the mammography apparatus 10 receives the power-off signal from the console 12, the supply of power to the power supply unit 48A of the projector 48 is cut off to turn off the power supply unit 48A.

As described above, in a case in which the console 12 according to this embodiment receives the instruction for the next imaging, the projector 48 is kept on, which makes it possible to immediately start the projection of the projection image P. Further, in a case in which the instruction for the next imaging is not received, the projector 48 is turned off, which makes it possible to suppress heat accumulation in the mammography apparatus 10.

Then, in Step S124, the detection unit 62 ends the acquisition of the height of the compression plate 40 started in Step S106. Specifically, the detection unit 62 ends the performance of the process in Step S106, and the acquisition of the movement signal and the derivation of the height of the compression plate 40 repeated at predetermined intervals.

Then, in Step S126, the detection unit 62 stops the counting of the timer 55 and resets the count. In a case in which the process in Step S126 ends, the projection control process illustrated in FIG. 5 ends.

In contrast, in a case in which the compression of the breast is completed, the user instructs the emission of the radiation R. In a case in which the mammography apparatus 10 receives an instruction to emit the radiation R, the radiation R is emitted from the radiation source 37R of the radiation emitting unit 37, and the radiation detector 28 captures a radiographic image of the breast. In a case in which the imaging ends, the user moves the compression plate 40 in the release direction to release the compression of the breast.

As described above, the console 12 according to this embodiment performs control to stop the projection of the projection image P onto the projection surface 45 in a case in which the height of the compression plate 40 does not change for a predetermined period or more. In other words, the console 12 performs control to stop the projection of the projection image P onto the projection surface 45 in a case in which the thickness of the breast compressed by the compression plate 40 does not change for a predetermined period or more or in a case in which the gap between the imaging table 30 and the compression plate 40 does not change for a predetermined period or more. In this way, the console 12 according to this embodiment performs control to stop the projection of the projection image P onto the projection surface 45 in a case in which the compression of the breast by the compression plate 40 is completed. Therefore, according to the console 12 of this embodiment, it is possible to immediately stop the projection of the projection image P after the compression of the breast ends.

Second Embodiment

In this embodiment, an aspect in which the projection of the projection image P is stopped by a standard different from that in the first embodiment will be described.

Figure 7:
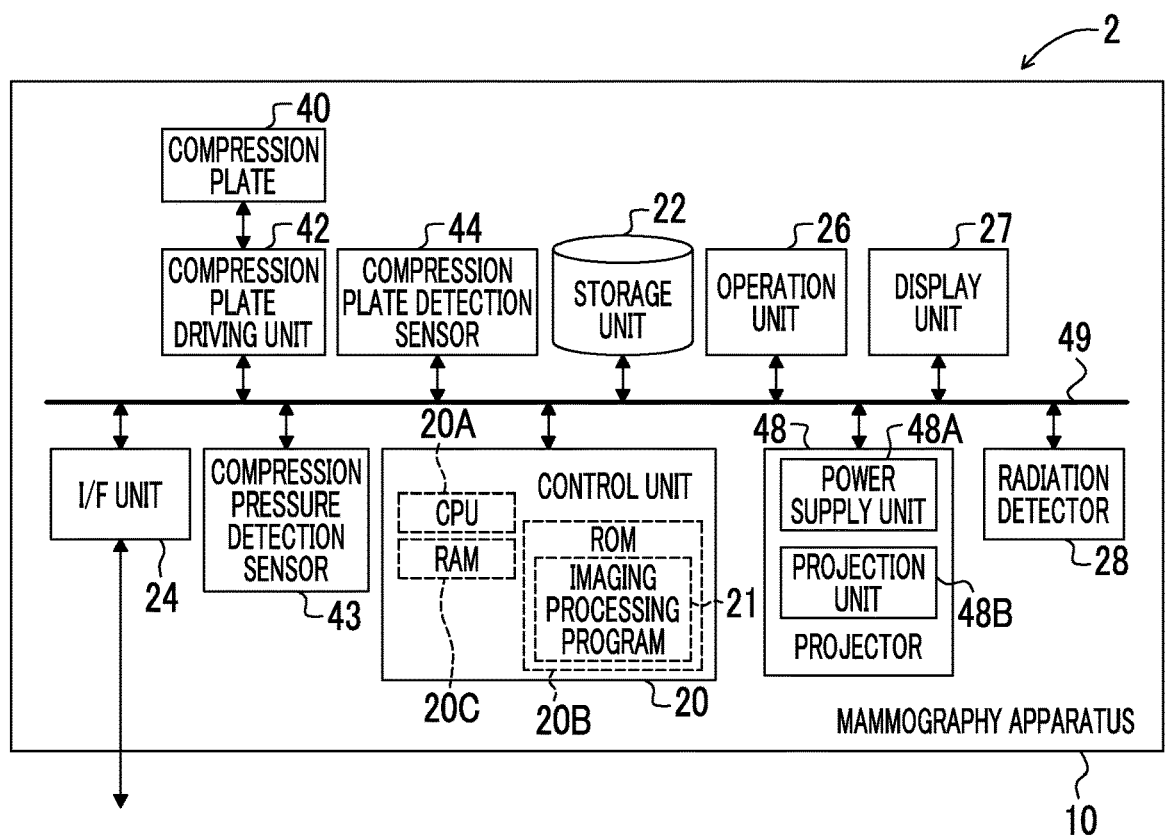
FIG. 7 is a block diagram illustrating an example of the configuration of a mammography apparatus according to a second embodiment.

In addition, the configuration of a mammography apparatus 10 according to this embodiment is partially different from that of the mammography apparatus 10 according to the first embodiment. FIG. 7 is a functional block diagram illustrating an example of the configuration of the mammography apparatus 10 according to this embodiment. As illustrated in FIG. 7, the mammography apparatus 10 according to this embodiment differs from the mammography apparatus 10 (see FIG. 3) according to the first embodiment in that it further comprises a compression pressure detection sensor 43.

The compression pressure detection sensor 43 has a function of detecting compression pressure related to the compression plate 40. For example, the compression pressure detection sensor 43 according to this embodiment is provided in the compression unit 36, detects the compression pressure, which is pressure related to the compression plate 40, and outputs a compression pressure signal indicating the detected compression pressure to the console 12 through the I/F unit 24. Examples of the compression pressure detection sensor 43 include a semiconductor-type pressure sensor, a capacitance-type pressure sensor, and a strain gauge such as a load cell. Further, the compression force of the compression plate 40 against the entire breast or compression pressure, which is compression force per unit area, may be applied as the compression pressure.

On the other hand, in the console 12 according to this embodiment, some of the functions of the detection unit 62 are different from those of the detection unit 62 according to the first embodiment. The detection unit 62 according to this embodiment has a function of detecting a case in which the compression pressure of the compression plate 40 against the breast does not change for a predetermined period or more as a case in which the compression of the breast by the compression plate 40 is completed. As described above, for example, in this embodiment, in a case in which the compression of the breast is completed, the user stops the movement of the compression plate 40. The compression pressure applied to the compression plate 40 gradually increases until compression is completed after the compression plate 40 comes into contact with the breast. However, in a case in which the movement of the compression plate 40 is stopped, the compression pressure related to the compression plate 40 hardly changes. For this reason, in this embodiment, the case in which the compression pressure of the compression plate 40 against the breast does not change for a predetermined period or more is regarded as the case in which the compression of the breast is completed. Therefore, the detection unit 62 detects whether or not the compression pressure has not changed for a predetermined period or more on the basis of the compression pressure signal input from the mammography apparatus 10. Then, the detection unit 62 detects the case in which the compression pressure does not change for a predetermined period or more as the case in which the compression of the breast by the compression plate 40 is completed. For example, the predetermined period in this embodiment is the same as that in the first embodiment, but is not particularly limited.

Figure 8:
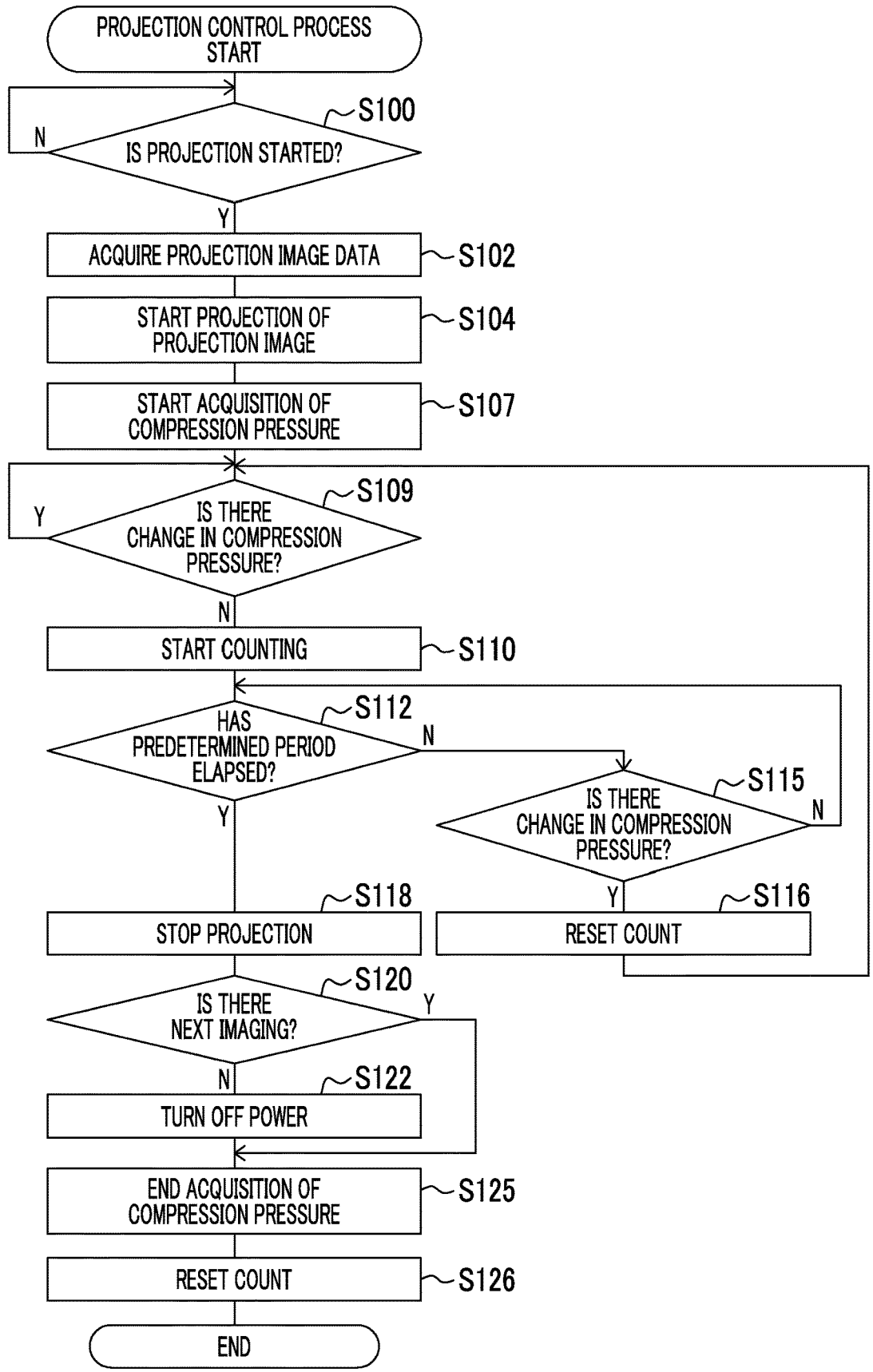
FIG. 8 is a flowchart illustrating an example of the flow of a projection control process according to the second embodiment.

Further, since this embodiment differs from the first embodiment in the projection control process performed in the console 12, the projection control process according to this embodiment will be described. FIG. 8 is a flowchart illustrating an example of the flow of the projection control process performed in the console 12 according to this embodiment.

As illustrated in FIG. 8, the projection control process according to this embodiment differs from the projection control process (see FIG. 5) according to the first embodiment in that it comprises processes in Steps S107, S109, S115, and S125 instead of the processes in Steps S106, S108, S114, and S124.

As illustrated in FIG. 8, in Step S107, the detection unit 62 according to this embodiment starts the acquisition of the compression pressure signal output from the mammography apparatus 10 to start the acquisition of the compression pressure. After that, the detection unit 62 repeatedly performs the acquisition of the compression pressure signal at predetermined intervals.

Then, in Step S109, the detection unit 62 determines whether or not the compression pressure has changed. The determination result in Step S109 is "Yes" until the compression pressure corresponding to the compression pressure signal does not change. On the other hand, in a case in which the compression pressure corresponding to the compression pressure signal has not changed, the determination result in Step S109 is "No", and the process proceeds to Step S110.

Further, in Step S115, the detection unit 62 determines whether or not the compression pressure has changed. In a case in which the compression pressure corresponding to the compression pressure signal has changed, the determination result in Step S115 is "Yes", and the process proceeds to Step S116. On the other hand, in a case in which the compression pressure corresponding to the compression pressure signal has not changed in Step S115, the determination result in Step S115 is "No", and the process returns to Step S112.

As described above, in this embodiment, the processes in Steps S109 to S116 are repeated until a predetermined period elapses after the compression pressure does not change. In a case in which the compression of the breast by the compression plate 40 is completed, as described above, the compression pressure related to the compression plate 40 does not change, and the detection unit 62 detects that the compression of the breast by the compression plate 40 is completed.

In addition, in Step S125, the detection unit 62 ends the acquisition of the compression pressure started in Step S107. Specifically, the detection unit 62 ends the performance of the process in Step S107 and the acquisition of the compression pressure signal repeated at predetermined intervals.

As described above, the console 12 according to this embodiment performs control to stop the projection of the projection image P onto the projection surface 45 in a case in which the compression pressure of the compression plate 40 against the breast does not change for a predetermined period or more. Therefore, similarly to the console 12 according to the first embodiment, the console 12 according to this embodiment performs control to stop the projection of the projection image P onto the projection surface 45 in a case in which the compression of the breast by the compression plate 40 is completed. Therefore, it is possible to immediately stop the projection of the projection image P after the compression of the breast is completed.

Third Embodiment

In this embodiment, an aspect in which the projection of the projection image P is stopped by a standard different from that in the first embodiment will be described.

In addition, the configurations of the mammography apparatus 10 and the console 12 according to this embodiment are the same as those in the first embodiment except that some of the functions of the receiving unit 60, the detection unit 62, and the control unit 64 of the console 12 are different. Therefore, the description of the same configurations will not be repeated.

The receiving unit 60 according to this embodiment further has a function of receiving an instruction to emit the radiation R. Specifically, the receiving unit 60 receives the instruction to emit the radiation R input by the user through the operation unit 56.

Further, the detection unit 62 according to this embodiment has a function of detecting a case in which the receiving unit 60 receives the instruction to emit the radiation R as the case in which the compression of the breast by the compression plate 40 is completed. After the compression of the breast is completed, the user leaves the mammography apparatus 10 and inputs the instruction to emit the radiation R. Then, the detection unit 62 according to this embodiment detects the case in which the receiving unit 60 receives the instruction to emit the radiation R as the case in which the compression is completed.

Further, the control unit 64 according to this embodiment further performs control to direct the radiation source 37R of the radiation emitting unit 37 to emit the radiation R in response to the instruction to emit the radiation R received by the receiving unit 60.

Figure 9:
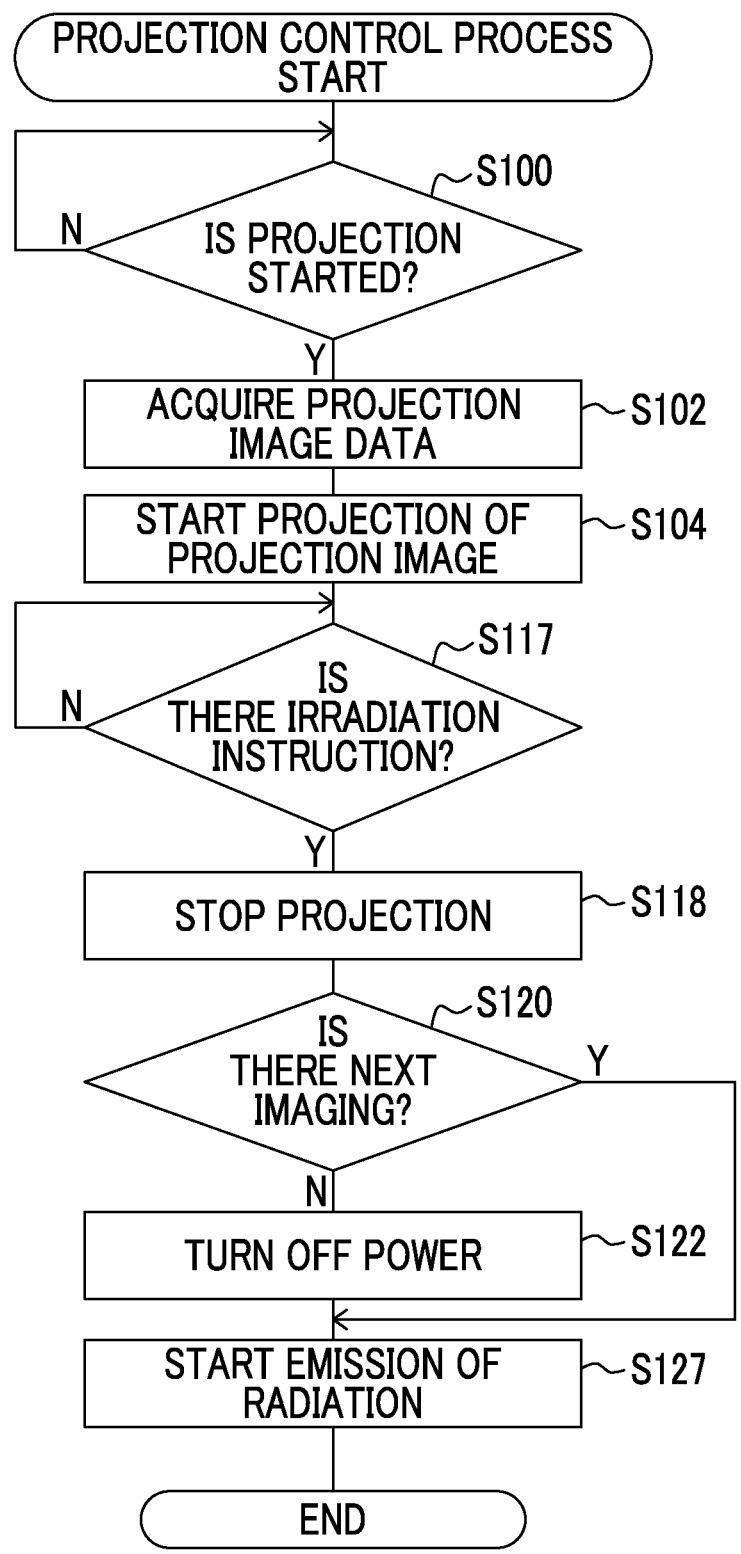
FIG. 9 is a flowchart illustrating an example of the flow of a projection control process according to a third embodiment.

Further, since this embodiment differs from the first embodiment in the projection control process performed in the console 12, the projection control process according to this embodiment will be described. FIG. 9 is a flowchart illustrating an example of the flow of the projection control process performed in the console 12 according to this embodiment.

As illustrated in FIG. 9, the projection control process according to this embodiment differs from the projection control process (see FIG. 5) according to the first embodiment in that it comprises a process in Step S117 instead of the processes in Steps S106 and S116 and comprises a process in Step S127 instead of the processes in Steps S124 and S126.

As illustrated in FIG. 9, the projection image data 53 is output to the mammography apparatus 10 through the I/F unit 54 in Step S104, and the detection unit 62 determines whether or not the receiving unit 60 receives the instruction to emit the radiation R in the next Step S117 in which the projection of the projection image P is started. The determination result in Step S117 is "No" until the receiving unit 60 receives the instruction to emit the radiation R. On the other hand, in a case in which the receiving unit 60 receives the instruction to emit the radiation R, the determination result in Step S117 is "Yes", and the process proceeds to Step S118. In this case, as described above, the detection unit 62 detects that the compression of the breast by the compression plate 40 is completed.

Further, in Step S127, the control unit 64 further performs control to direct the radiation source 37R of the radiation emitting unit 37 to emit the radiation R in response to the instruction to emit the radiation R received by the receiving unit 60. Then, in the mammography apparatus 10, the control unit 20 directs the radiation source 37R to emit the radiation R. In a case in which the process in Step S127 ends, the projection control process illustrated in FIG. 9 ends.

As described above, the console 12 according to this embodiment performs control to stop the projection of the projection image P onto the projection surface 45 in a case in which the instruction to emit the radiation R is received. Therefore, similarly to the console 12 according to the first embodiment, the console 12 according to this embodiment performs control to stop the projection of the projection image P onto the projection surface 45 in a case in which the compression of the breast by the compression plate 40 is completed. Therefore, it is possible to immediately stop the projection of the projection image P after the compression of the breast is completed.

In addition, in this embodiment, after the projection of the projection image P is stopped, the radiation R is emitted. However, the present disclosure is not limited to this aspect. For example, after the radiation R is emitted, the projection of the projection image P may be stopped.

Fourth Embodiment

In this embodiment, an aspect in which a mode for capturing a radiographic image is different from that in the first embodiment will be described. In each of the above-described embodiments, the aspect in which the mammography apparatus 10 captures one radiographic image has been described. However, in this embodiment, an aspect in which the mammography apparatus 10 captures each of a series of a plurality of radiographic images will be described.

In this embodiment, an aspect in which CC imaging is continuously performed for each of the left and right breasts of the subject will be described as an example of the capture of each of a series of a plurality of radiographic images. Hereinafter, CC imaging for the left breast is referred to as "LCC imaging", and CC imaging for the right breast is referred to as "RCC imaging".

In a case in which the sequential performance of the LCC imaging and the RCC imaging in this order is designated in the imaging menu, first, the LCC imaging is performed with the left breast of the subject compressed by the compression plate 40. In a case in which the LCC imaging ends, the compression of the left breast is released. Then, the RCC imaging is performed with the right breast of the subject being compressed by the compression plate 40. In a case in which the RCC imaging ends, the compression of the right breast is released. Then, the capture of each of a series of a plurality of radiographic images ends.

Since the configurations of the mammography apparatus 10 and the console 12 according to this embodiment are the same as the configurations of the mammography apparatus 10 and the console 12 (see FIG. 3) according to the first embodiment, the description thereof will not be repeated.

On the other hand, since this embodiment differs from the first embodiment in the projection control process performed in the console 12, the projection control process according to this embodiment will be described. FIG. 10 is a flowchart illustrating an example of the flow of the projection control process performed in the console 12 according to this embodiment.

As illustrated in FIG. 10, the projection control process according to this embodiment differs from the projection control process (see FIG. 5) according to the first embodiment in that it comprises processes in Steps S103 and S105 instead of the processes in Steps S102 and S104. Further, the projection control process according to this embodiment differs from the projection control process according to the first embodiment in that it comprises processes in Step S119 and Steps S100A to S118A.

For example, in this embodiment, each of a plurality of projection image data items indicating projection images P for LCC imaging and a plurality of projection image data items indicating projection images P for RCC imaging which correspond to the types of the compression plates 40 is stored as the projection image data 53 in the storage unit 52 so as to be associated with the compression plate identifier. Therefore, in the projection control process according to this embodiment, as illustrated in FIG. 10, in Step S103, the control unit 64 according to this embodiment acquires the projection image data 53 for LCC imaging and the projection image data 53 for RCC imaging which correspond to the compression plate identifier input from the detection unit 62 from the storage unit 52. In addition, it is preferable that each of the projection image P for LCC imaging and the projection image P for RCC imaging includes an image for displaying information indicating whether an object to be imaged is the left breast or the right breast.

Then, in Step S105, the control unit 64 outputs the projection image data 53 for LCC imaging acquired in Step S103 to the mammography apparatus 10 through the I/F unit 54. In the mammography apparatus 10, in a case in which the projection image data 53 for LCC imaging is input, the control unit 20 performs control to direct the projection unit 48B of the projector 48 to project the projection image P corresponding to the projection image data 53 for LCC imaging. A display image corresponding to the projection image P for LCC imaging is displayed on the projection surface 45 of the compression plate 40 attached to the compression unit 36 of the mammography apparatus 10 by this control.

Further, as illustrated in FIG. 10, in Step S119 after Step S118, the detection unit 62 stops the counting of the timer 55 and resets the count as in Step S126.

As described above, the user releases the compression of the left breast in a case in which the LCC imaging ends. Then, the right breast is positioned on the imaging table 30, and the compression plate 40 is moved in the compression direction to compress the breast. Then, in Step S100A, the control unit 64 determines whether or not to start the projection of the projection image P as in Step S100. The determination result in Step S100A is "No" until the receiving unit 60 receives the projection start instruction signal. On the other hand, in a case in which the receiving unit 60 receives the projection start instruction signal, the determination result in Step S100A is "Yes", and the process proceeds to Step S105A.

In Step S105A, the control unit 64 outputs the projection image data 53 for RCC imaging acquired in Step S103 to the mammography apparatus 10 through the I/F unit 54. In the mammography apparatus 10, in a case in which the projection image data 53 for RCC imaging is input, the control unit 20 performs control to direct the projection unit 48B of the projector 48 to project the projection image P corresponding to the projection image data 53 for RCC imaging. A display image corresponding to the projection image P for RCC imaging is displayed on the projection surface 45 of the compression plate 40 attached to the compression unit 36 of the mammography apparatus 10 by this control.

Processes in the next Steps S108A to S116A are repeated until a predetermined period elapses after the height of the compression plate 40 does not change as in Steps S108 to S116.

In a case in which a predetermined period has elapsed since the height of the compression plate 40 did not change, in Step S118A, the control unit 64 outputs the stop control signal for stopping the projection of the projection image P by the projector 48 to the mammography apparatus 10 through the I/F unit 54 as in Step S118. In the mammography apparatus 10, in a case in which the stop control signal is input, the control unit 20 stops the projection of the projection image P by the projection unit 48B of the projector 48. Specifically, the emission of the projection light for projecting the projection image P is stopped.

As described above, in a case in which a series of a plurality of radiographic images are captured, the console 12 according to this embodiment performs control to stop the projection of the projection image P between the operations of capturing each radiographic image and to project the projection image P corresponding to the capture of each radiographic image onto the projection surface 45 of the compression plate 40. Therefore, similarly to the console 12 according to the first embodiment, the console 12 according to this embodiment performs control to stop the projection of the projection image P onto the projection surface 45 in a case in which the compression of the breast by the compression plate 40 is completed. Therefore, it is possible to immediately stop the projection of the projection image P after the compression of the breast is completed.

In addition, in this embodiment, the aspect has been described in which the projection image P for RCC imaging is projected in a case in which the receiving unit 60 receives the projection start instruction signal based on the projection start instruction from the user. However, the timing when the projection image P for RCC imaging is projected is not limited to this aspect. For example, after the projection of the projection image P for LCC imaging is stopped, the projection image P for RCC imaging may be projected immediately. Further, for example, the projection image P for RCC imaging may be projected at the timing when the compression of the left breast by the compression plate 40 is released or at the timing when the compression of the right breast by the compression plate 40 is started.

As described above, the console 12 according to each of the embodiments comprises the CPU 50A, which corresponds to at least one processor. The CPU 50A detects whether or not the compression of the breast by the compression plate 40 in the mammography apparatus 10 is completed. In addition, in a case in which the CPU 50A detects that the compression is completed, it performs control to direct the projector 48, which projects the projection image P onto the projection surface 45 of the compression plate 40, to stop the projection of the projection image P onto the projection surface 45.

As described above, the console 12 according to each of the above-described embodiments performs control to stop the projection of the projection image P onto the projection surface 45 in a case in which the compression of the breast by the compression plate 40 is completed. Therefore, according to the console 12 of each of the above-described embodiments, the projection image P is projected onto the projection surface 45 of the compression plate 40 while the user is performing an operation of compressing the breast of the subject with the compression plate 40 and is performing positioning. In a case in which the positioning ends and the compression of the breast is completed, the projection of the projection image P is stopped immediately. Since the projection of the projection image P is stopped immediately, it is possible to suppress heat accumulation in the projector 48 and to suppress power consumption. Therefore, according to the console 12 of each of the above-described embodiments, it is possible to automatically stop the projection of the projection image P onto the projection surface 45 of the compression plate 40 at an appropriate timing.

In each of the above-described embodiments, the aspect in which the projection of the projection image P by the projector 48 is started in a case in which the user instructs the start of projection has been described. However, the timing when the projection of the projection image P is started is not limited to this aspect. For example, the projection may be started at the timing when an imaging menu is instructed from the console 12 to the mammography apparatus 10.

Further, the configuration for projecting the projection image P in the mammography apparatus 10 is not limited and is not limited to the aspect using the projector 48 described in each of the above-described embodiments. Further, in a case in which the projector 48 is applied, the configuration of the projector 48 is not limited. For example, in each of the above-described embodiments, the aspect in which the projection image P projected from the projector 48 is directly projected onto the projection surface 45 has been described. However, the projection image P may be reflected from a mirror or the like to be projected onto the projection surface 45. In this case, the direction in which the projection image P is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P onto the projection surface 45. Specifically, in a case in which the projection of the projection image P is started, control is performed such that the shutter is opened to transmit the projection light. On the other hand, in a case in which the projection of the projection image P is ended, control is performed such that the shutter is closed to block the projection light.

Further, in each of the above-described embodiments, the power supply unit 48A of the projector 48 may be turned on before the projection image P is projected, and the specific timing when the power supply unit 48A is turned on is not limited, which is not described above. For example, the power supply unit 48A may be turned on immediately after the projection control process is started in the console 12 or immediately before the projection image P is projected.

Further, in each of the above-described embodiments, the aspect in which a projection image for displaying an image for guiding at least one of the shape or position of the breast on the projection surface 45 of the compression plate 40 is applied as the projection image P has been described. However, the projection image P is not limited to this aspect. For example, the projection image P may be a projection image for displaying information related to the subject, such as the name of the subject, and information related to compression, such as compression pressure or the height of the compression plate 40, on the projection surface 45 of the compression plate 40. In addition, the projection image P may be a projection image for displaying a plurality of information items. Further, the projection image P may be a radiographic image of the breast.

Further, in each of the above-described embodiments, the image indicating the skin line of the breast and the position of the nipple in a case in which a standard breast is compressed into an ideal state is applied as the projection image P. However, the projection image P is not limited to this aspect. For example, the projection image P may be the radiographic image of the breast of the same subject captured in the past, an image indicating a skin line generated from the radiographic image captured in the past, or the like. In addition, a method for generating the image indicating the skin line is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line. Furthermore, the projection image P may be, for example, information related to the current imaging, such as an imaging date and time or a radiographer, information related to the past imaging, such as compression pressure in the past imaging, and information related to the subject, such as the name of the subject. Alternatively, the projection image P may be an image indicating characters or numbers.

Further, in each of the above-described embodiments, the aspect in which the size of the projection image P is equal to or less than the size of the projection surface 45 has been described. However, the size of the projection image P may be equal to or greater than the size of the projection surface 45 of the compression plate 40. That is, the projection image P may be projected onto the imaging surface 30A of the imaging table 30. Furthermore, the projection image P may be projected only on the imaging table 30. Further, for example, the projection image P may be displayed on the wall portion 41B of the compression plate 40.

Further, in each of the above-described embodiments, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the receiving unit 60, the detection unit 62, and the control unit 64.

Further, in each of the above-described embodiments, for example, the following various processors can be used as the hardware structure of processing units performing various processes such as the receiving unit 60, the detection unit 62, and the control unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the projection control program 51 is stored (installed) in the ROM 50B in advance has been described. However, the present disclosure is not limited thereto. The projection control program 51 may be recorded on a recording medium, such as a compact disc read only memory (CD-ROM), a digital versatile disc read only memory (DVD-ROM), or a universal serial bus (USB) memory, and then provided. In addition, the projection control program 51 may be downloaded from an external device through a network.

What is claimed is:

1. A control device comprising:
at least one processor that is configured to
detect whether or not compression of a breast by a compression member in a mammography apparatus is completed and
perform control to direct an image projection unit, which projects a projection image onto a projection surface of the compression member, to stop the projection of the projection image onto the projection surface in a case in which it is detected that the compression is complete;
wherein the case in which the compression is completed is a case in which a compression pressure of the compression member against the breast does not change for a predetermined period or more.

2. The control device according to claim 1,
wherein the case in which the compression is completed is also a case in which a gap between an imaging table on which the breast is positioned and the compression member does not change for a predetermined period or more.

3. The control device according to claim 1,
wherein the case in which the compression is completed is also a case in which a thickness of the breast compressed by the compression member does not change for a predetermined period or more.

4. The control device according to claim 1,
wherein the processor is configured to receive an irradiation start instruction to start irradiation of the breast with radiation, and
the case in which the compression is completed is also a case in which the processor receives the irradiation start instruction.

5. The control device according to claim 4,
wherein, after performing the control to stop the projection, the processor is configured to perform control to direct the mammography apparatus to start the irradiation of the breast with the radiation.

6. The control device according to claim 1,
wherein the processor is configured to perform control to turn off the image projection unit to stop the projection of the projection image onto the projection surface.

7. The control device according to claim 6,
wherein the processor is configured to perform control to stop the projection of the projection image onto the projection surface without turning off the image projection unit in a case in which an instruction for next imaging using the mammography apparatus is received.

8. The control device according to claim 1,
wherein, in a case in which the mammography apparatus captures each of a series of a plurality of radiographic images, the processor is further configured to perform control to direct the image projection unit to stop the projection of the projection image onto the projection surface between imaging operations corresponding to each of the plurality of radiographic images and further perform control to project, onto the projection surface, the projection image corresponding to each of the imaging operations corresponding to the plurality of radiographic images.

9. A control method comprising:
detecting whether or not compression of a breast by a compression member in a mammography apparatus is completed; and
performing control to direct an image projection unit, which projects a projection image onto a projection surface of the compression member, to stop the projection of the projection image onto the projection surface in a case in which it is detected that the compression is complete;
wherein the case in which the compression is completed is a case in which a compression pressure of the compression member against the breast does not change for a predetermined period or more.

10. A non-transitory computer-readable storage medium storing a control program that causes a computer to perform a process comprising:
detecting whether or not compression of a breast by a compression member in a mammography apparatus is completed; and
performing control to direct an image projection unit, which projects a projection image onto a projection surface of the compression member, to stop the projection of the projection image onto the projection surface in a case in which it is detected that the compression is complete;
wherein the case in which the compression is completed is a case in which a compression pressure of the compression member against the breast does not change for a predetermined period or more.

* * * * *